(12) United States Patent
Chaput et al.

(10) Patent No.: US 8,685,894 B2
(45) Date of Patent: Apr. 1, 2014

(54) MODIFIED NUCLEIC ACID NANOARRAYS AND USES THEREFOR

(75) Inventors: John Chaput, Phoenix, AZ (US); Stuart Lindsay, Phoenix, AZ (US); Hao Yan, Chandler, AZ (US); Peiming Zhang, Gilbert, AZ (US)

(73) Assignee: Arizona Board of Regents, A body Corporate of the State of Arizona Acting for and on behalf of Arizona State University, Scottsdale, AZ (US)

( * ) Notice: Subject to any disclaimer, the term of this patent is extended or adjusted under 35 U.S.C. 154(b) by 892 days.

(21) Appl. No.: 12/301,884

(22) PCT Filed: May 23, 2007

(86) PCT No.: PCT/US2007/012323
§ 371 (c)(1),
(2), (4) Date: May 7, 2010

(87) PCT Pub. No.: WO2007/139849
PCT Pub. Date: Dec. 6, 2007

(65) Prior Publication Data
US 2010/0216658 A1      Aug. 26, 2010

Related U.S. Application Data

(60) Provisional application No. 60/808,335, filed on May 25, 2006.

(51) Int. Cl.
*C40B 40/06* (2006.01)

(52) U.S. Cl.
USPC .......................................................... 506/16

(58) Field of Classification Search
None
See application file for complete search history.

(56) References Cited

U.S. PATENT DOCUMENTS

| | | |
|---|---|---|
| 6,255,469 B1 | 7/2001 | Seeman |
| 2004/0248144 A1 | 12/2004 | Mir |
| 2005/0118625 A1 | 6/2005 | Mounts |

FOREIGN PATENT DOCUMENTS

| | | |
|---|---|---|
| WO | WO 97/41142 | 11/1997 |
| WO | WO 2006/124089 | 11/2006 |

OTHER PUBLICATIONS

Park et al. (Dec. 22, 2005) Angewandte Chemie International Edition vol. 45 pp. 735 to 739.*
Lee et al. (Oct. 14, 2005) Analytical Chemistry vol. 77 pp. 7832 to 7837.*
Yan. DNA-Templated Self-Assembly of Protein Arrays and Highly Conductive Nanowires. Science (2003) 301:1882-1884.
Seeman. At the Crossroads of Chemistry, Biology, and Materials: Structural DNA Nanotechnology. Chem. Biol. (2003) 10:1151-59.
Seeman. DNA in a material world. Nature (2003) 421:427-431.
Winfree. Design and self-assembly of two-dimensional DNA crystals. Nature (1998) 394: 539-544.
Fu. DNA double-crossover molecules. Biochemistry (1993) 32:3211-20.
Seeman. Nucleic acid junctions and lattices. J. Theor. Biol. (1982) 99:237-47.
Storhoff. Programmed Materials Synthesis with DNA. Chem. Rev. (1999) 99:1849-1862.
Yan. Directed nucleation assembly of DNA tile complexes for barcode-patterned lattices. Proc. Natl. Acad. Sci. USA (2003) 100:8103-8108.
Seeman. De novo design of sequences for nucleic acid structural engineering. J. Biomol. Struct. Dyn. (1990) 8:573-81.

* cited by examiner

*Primary Examiner* — Christian Boesen
(74) *Attorney, Agent, or Firm* — McDonnell Boehnen Hulbert & Berghoff LLP (57) ABSTRACT

The present invention provides finite, addressable, and self-assembling nucleic acid tiling arrays, and methods for their use.

11 Claims, 2 Drawing Sheets

MODIFIED NUCLEIC ACID NANOARRAYS AND USES THEREFOR

CROSS-REFERENCE

The present invention claims priority to U.S. Provisional Patent Application Ser. No. 60/808,335 filed May 25, 2006, which is incorporated by reference herein in its entirety.

FIELD OF THE INVENTION

The present invention relates to the fields of nucleic acid-based tiling arrays, gene expression arrays, and related methods.

BACKGROUND OF THE INVENTION

Current macroscopic arrays rely on large quantities of material extracted by PCR from target cells using fluorescent primers to label the target DNA. We have recently disclosed a method for making nanoscale arrays from self-assembly of DNA in such a way as to expose single stranded probes. (WO2006/124089 published Nov. 23, 2006, incorporated by reference herein in its entirety) The present invention provides improvements allowing these and other nucleic acid tiling arrays to be used directly inside the contents of single cells or with very small volumes of sample.

SUMMARY OF THE INVENTION

The present invention provides finite, addressable, and self-assembling nucleic acid tiling arrays comprising addressable nucleic acid probes and one or more unique chemical tags.

The present invention further provides finite, addressable, and self-assembling nucleic acid tiling arrays, wherein one or more nucleic acid probes on the nucleic acid tiling array is modified to permit specific bonding and/or cross-linking of captured targets to the nucleic acid probes.

The present invention further provides finite, addressable, and self-assembling nucleic acid tiling arrays comprising addressable nucleic acid probes, wherein one or more of the nucleic acid probes comprises 2'-5' DNA.

The present invention further provides finite, addressable and self-assembling nucleic acid arrays of any of the above embodiments, wherein the nucleic acid probes comprise pairs of single stranded nucleic acids arranged to permit a pair of single stranded nucleic acids to both hybridize to the same target. In a preferred embodiment, the pair of single stranded nucleic acids are arranged to permit formation of a continuous double helix after hybridization to the comprising the pair of single stranded nucleic acids and the target The present invention further provides methods for gene expression analysis, comprising incubating a sample containing mRNA to be analyzed with one or more nucleic acid tiling arrays of the invention comprising 2'-5' DNA, under conditions wherein the 2'-5'-containing nucleic acid probes can hybridize with mRNA targets in the sample; isolating the nucleic acid tiling arrays; and analyzing binding events on the nucleic acid tiling arrays.

DETAILED DESCRIPTION OF THE INVENTION

As used herein, the singular forms "a", "an" and "the" include plural referents unless the context clearly dictates otherwise. For example, reference to a "nucleic acid" means one or more nucleic acids.

In one aspect, the present invention provides finite, addressable, and self-assembling nucleic acid tiling arrays comprising addressable nucleic acid probes and one or more unique chemical tags. One or more unique chemical tags (5 in FIG. 2) are added to a finite, addressable, and self-assembling nucleic acid tiling array comprising addressable nucleic acid probes, permitting easy extraction of the nucleic acid tiling arrays from a complex environment, including but not limited to an assembly mixture, cells, and cell extracts. In a preferred embodiment, a tag is added at one or both ends of the nucleic acid tiling array, although the tag(s) can be added elsewhere on the array, in addition to or instead of the ends. For example, a unique chemical tag could be attached to one end of a protruding single strand of DNA, positioned on the array according to the finite, addressable, and self-assembling tiling arrays described in WO2006/124089. The one or more tags can be attached to a base on the array using a specifically-modified base incorporated into one of the oligonucleotides used for assembly of the array. Similarly, a modified sugar could be incorporated during synthesis of one of the oligonucleotides comprising the array. Such chemical tags can be used, for example, to facilitate isolation of the nucleic acid tiling array from complex mixtures.

As used herein, "nucleic acid" means DNA, RNA, peptide nucleic acids ("PNA"), 2'-5' DNA (a synthetic material with a shortened backbone that has a base-spacing that matches the A conformation of DNA; 2'-5' DNA will not normally hybridize with DNA in the B form, but it will hybridize readily with RNA) and locked nucleic acids ("LNA"), nucleic acid-like structures, as well as combinations thereof and analogues thereof. Nucleic acid analogues include known analogues of natural nucleotides which have similar or improved binding properties. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs), methylphosphonate linkages or alternating methylphosphonate and phosphodiester linkages (Strauss-Soukup (1997) Biochemistry 36:8692-8698), and benzylphosphonate linkages, as discussed in U.S. Pat. No. 6,664,057; see also Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS1992); Milligan (1993) J. Med. Chem. 36:1923-1937; Antisense Research and Applications (1993, CRC Press).

As used herein, a "nucleic acid tiling array" is an assembled array of nucleic acid tiles, including, but not limited to all embodiments and aspects of the nucleic acid tiles and arrays disclosed in WO2006/124089, as well as 4 arm branch junctions, 3 arm branch junctions, double crossovers; triple crossovers, parallelograms, 8 helix bundles, 6-tube formations, and nucleic acid tiles prepared from such nucleic acid tiles (Yan, H. et al., Science 2003, 301, 1882-1884; U.S. Pat. No. 6,255,469; WO 97/41142; Seeman, N. C., Chem Biol, 2003. 10: p. 1151-9; Seeman, N. C. N., 2003. 421: p. 427-431; Winfree, E. et al., Nature, 1998. 394: p. 539-44; Fu, T. J. and N. C. Seeman, Biochemistry, 1993. 32: p. 3211-20; Seeman, N. C., J Theor Biol, 1982. 99: p. 237-47; Storhoff, J. J. and C. A. Mirkin, Chem. Rev., 1999. 99: p. 1849-1862; Yan et al., Proceedings of the National Academy of Sciences 100, Jul. 8, 2003 pp 8103-8108, and WO2006/124089.)

As used herein, the term "nucleic acid probe" refers to nucleic acid sequences synthesized as part of one or more polynucleotide structure in a nucleic acid tile that does not participate in base pairing with other polynucleotide structures within a nucleic acid tile or with adjacent nucleic acid tiles in a nucleic acid tiling array (See, for example, WO2006/124089). Thus, the nucleic acid probe is available for interactions with various "targets" to which it binds directly or indirectly. Such targets include, but are not limited to, nucleic acids (RNA or DNA), polypeptides, lipids, carbohydrates, other organic molecules, inorganic molecules, metallic particles, magnets, quantum dots, and combinations thereof. In one embodiment, the nucleic acid probe comprises a DNA probe. The use of nucleic acid probes as disclosed herein allows a wide variety of discrete molecules to be placed at precise locations on the nucleic acid tiling array with nm-scale accuracy, and thus has widespread use in, for example, the fields of nanoelectronics, nanomechanical devices, biosensors, programmable/autonomous molecular machines, and molecular computing systems. Thus, in a further embodiment, the nucleic acid tiling arrays further comprise a plurality of targets bound to nucleic acid probes specific for those targets.

The particular nucleic acid probe sequence, length, or structure is not critical to the invention; the only requirement is that the nucleic acid probe be able to bind, directly or indirectly, one or more targets of interest. The nucleic acid probe may be single stranded, single stranded but subject to internal base pairing, or double stranded, and the nucleic acid probe may be of any length that is appropriate for the design of the nucleic acid tile of which the nucleic acid probe is a part, but constrained in length so that neighboring probes (either within a tile or between different tiles) do not interfere with target binding by the nucleic acid probe.

As will be apparent to those of skill in the art, in this embodiment, not all of the nucleic acid tiles in the nucleic acid tiling array are required to possess a nucleic acid probe. Thus, one or more of the nucleic acid tiles in the nucleic acid tiling array comprises a nucleic acid probe; more preferably a majority of the nucleic acid tiles in the array comprise a nucleic acid probe; more preferably all of the nucleic acid tiles comprise a nucleic acid probe with the optional exception of a small percentage of the nucleic acid tiles to serve as control tiles.

As will also be apparent to those of skill in the art, based on the teachings herein, the nucleic acid probe-containing tiles in an array may all contain the same nucleic acid probe; may all contain different nucleic acid probes, or a mixture thereof. Thus, the targets for binding to the nucleic acid probes can be the same for all nucleic acid tiles in a given nucleic acid tiling array, all different, or mixtures thereof. In a further embodiment, each of the nucleic acid probe-containing nucleic acid tiles comprises more than one nucleic acid probe.

The probes may bind to a target of interest either directly or indirectly, or a combination thereof. As used herein, "direct binding" means that the target binds directly to the nucleic acid probe. Such binding can be of any type, including base pairing with nucleic acids, or other interactions. Preferred targets for direct interaction include nucleic acids (DNA and RNA whether single stranded or double stranded; DNAzymes, aptameric sensors, signaling aptamers), polypeptides, lipids, carbohydrates, other organic molecules, inorganic molecules (including but not limited to insulators, conductors, semi-conductors, magnetic particles, metallic particles, optical sensors, etc.), magnets, quantum dots, and any other type of molecule to which a nucleic acid probe (such as an aptamer) is capable of binding. As used herein, "indirect binding" means that the target binds to the nucleic acid probe through some intermediate molecule. One non-limiting example of indirect binding involves mRNA display, in which the mRNA portion of a genetically tagged polypeptide base pairs with the nucleic acid probe, resulting the polypeptide being presented at a precise location on the nucleic acid tile containing the complementary nucleic acid probe. Messenger RNA display involves production of mRNA-protein fusion molecules in vitro using the natural peptidyl transferase activity of the ribosome. In this reaction, messenger RNA is chemically modified to contain a puromycin residue at its 3'-end. During translation, the ribosome stalls upon reaching the DNA-puromycin linker, thereby enabling puromycin to enter the A-site and become covalently bound to the C-terminus of the nascent polypeptide chain in the adjoining P-site, thereby linking genotype and phenotype together in a single molecule. Other non-limiting examples would include chemical conjugation approaches that facilitate the formation of certain DNA-peptides, DNA-PNA, and PNA-Peptides, chimeric molecules, as well as other molecular biology approaches like ribosome display and DNA display. Those of skill in the art will recognize, based on the teachings herein, that any other molecules can be indirectly bound to the nucleic acid probe of the invention, including but not limited to nucleic acids (DNA and RNA whether single stranded or double stranded), lipids, carbohydrates, other organic molecules, inorganic molecules and metallic particles, magnets, and quantum dots. Conditions for binding the target to the nucleic acid probe will depend on the nature of the DNA probe and the target, but can be determined by those of skill in the art, based on the teachings herein.

Thus, the invention provides nucleic acid tiles comprising one or more unique chemical tags, wherein the nucleic acid tiles self-assemble into finite arrays (ie: known boundaries) of known morphology with one or more tiles displaying a nucleic acid probe that can directly or indirectly bind a target of interest. Because the position of each tile in the array is unambiguously defined, the present invention provides designer, high-density nanometer scale molecule arrays, where the molecules are present at precise, well-defined locations. Therefore, in various embodiments, the present invention further provides molecule arrays, comprising a nucleic acid tiling array of the invention, wherein a plurality of nucleic acid tiles in the nucleic acid tiling array comprise one or more nucleic acid probes, and wherein the one or more nucleic acid probes in the plurality of nucleic acid tiles is bound to a target, wherein the target is selected from the group consisting of nucleic acids (DNA and RNA whether single stranded or double stranded; DNAzyme, aptameric sensors, signaling aptamers), polypeptides, lipids, carbohydrates, other organic molecules, inorganic molecules (including but not limited to insulators, conductors, semi-conductors, magnetic particles, metallic particles, optical sensors, etc.), magnets, quantum dots, and any other type of molecule to which a nucleic acid probe (such as an aptamer) is capable of binding.

As used herein, "addressable" means that the nucleic acid probes are at specific and identifiable locations on the nucleic acid tiling array, and thus binding events occurring at individual nucleic acid probes can be specifically measured.

In a preferred embodiment of this first aspect, the nucleic acid tiling array comprises an indexing feature to orient the tiling array and thus facilitate identification of each individual nucleic acid tile in the array. Any indexing feature can be used, so long as it is located at some spot on the array that has a lower symmetry than the array itself. Examples of such indexing features include, but are not limited to:

including one or more tiles that impart(s) an asymmetry to the array;

including one or more tiles that is/are differentially distinguishable from the other tiles (for example, by a detectable label);

including any protrusion on an edge of the array that is offset from two edges by unequal amounts, which will serve to index the array even if it is imaged upside down;

including a high point on the array that is detectable;

introducing one or more gaps in the tiling array that introduce a detectable asymmetry; and making the nucleic acid tiling array of low enough symmetry with respect to rotations and inversions that locations on it could be identified unambiguously; for example, a nucleic acid tiling array in the shape of a letter "L" with unequal sized arms would serve such a purpose.

Figure 2:
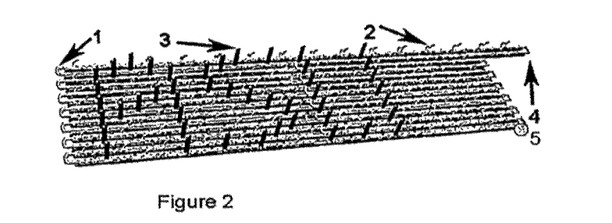
FIG. 2 is a diagram of an exemplary nucleic acid thread-strand based tiling array comprising a unique chemical tag.

FIG. 2 shows a nucleic acid thread-strand based tiling array as an example of a nucleic acid tiling array comprising a unique chemical tag. (See below for a detailed discussion of nucleic acid tiling arrays based on nucleic acid thread strands.) In this non-limiting example, a unique chemical tag can be added to the end of the thread strand 1. For example, the thread strand may be ligated to a nucleic acid modified with a biotin molecule. To do this, a short piece of DNA complementary to both one end of the thread strand and also to the nucleic acid labeled with biotin is used to generate a short length of double stranded DNA, so that a ligase can covalently join the biotinylated nucleic acid to the thread strand. In this way, the nucleic acid tiling array is now covalently tagged with a chemical marker (in this example, biotin) so that they can be easily isolated. Another embodiment of such chemical modifications is to hybridize a short biotinylated nucleic acid that has a psoralin molecule tethered to the other end of the nucleic acid by means of a PEG linker. This construct, when exposed to UV light, results in psoralin-mediated covalent joining of the two nucleic acid strands in the region where they form a duplex. In one embodiment, the nucleic acid strands comprise DNA. Similar modifications can be made using other chemical tags, and such chemical tags can be applied to any type of nucleic acid tiling array.

Figure 4:
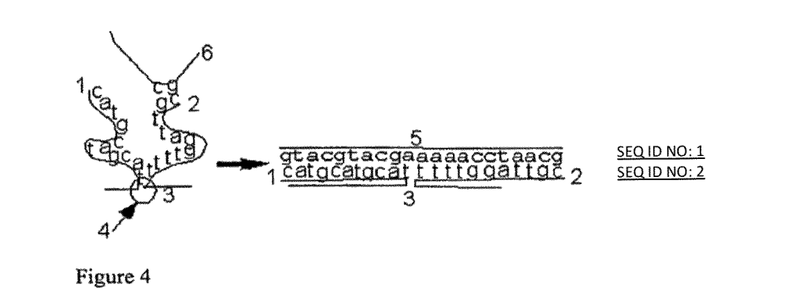
FIG. 4 is a diagram of an exemplary nucleic acid probe comprising a pair of single stranded nucleic acids, arranged so as to protrude from the nucleic acid tiling array and to permit the pairs of single stranded nucleic acids to take part in hybridization with a single target probe.

In another embodiment, nucleic acid probes comprise pairs of single stranded nucleic acids as illustrated in FIG. 4. The pair of single stranded nucleic acids (1,2) are arranged on the array so as to protrude from the array (3) at sites that are close enough to permit the pairs of single stranded nucleic acids to take part in hybridization with a single target probe. For example, a pair of single stranded nucleic acids can comprise or consist of a first nucleic acid and a second nucleic acid that are posited to permit formation of a double helix comprising or consisting of said first probe, said second probe and said target strand.

If needed, a small stem region in which probes 1 and 2 are paired (circles and labeled 4) can be incorporated. When a target sequence is present that is complementary to both probes 1 and 2, the structure shown on the right of FIG. 4 forms. The target is shown as 5. The result of this and only this type of hybridization is the formation of a rigid structure, readily visible in an atomic force microscope image. In case of non-specific adsorption, the rigid structure is not formed. An example is shown by the partial hybridization with a spurious target labeled 6. Thus probes of this design enable direct readout of specific adsorption by AFM and eliminate the problem of non-specific adsorption that would be detected with traditional, dye-based methods. The probes used for the sensing strands 1 and 2 are preferably made to be more than 10 bases each; more preferably at least 20 bases, which is a commonly-used probe size, giving exceptional specificity and an easily recognized feature in an atomic-force microscope-based readout.

Figure 3:
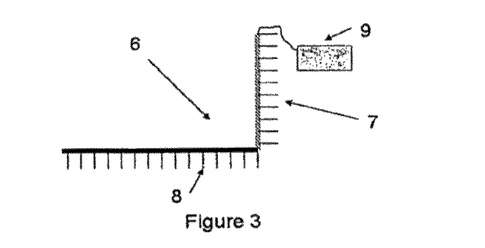
FIG. 3 is a diagram of an exemplary modification of nucleic acid probes to allow specific bonding and/or cross-linking of captured targets.

In a second embodiment, nucleic acid probes on the nucleic acid tiling arrays are modified so as to allow specific bonding and/or cross-linking of captured targets to the nucleic acid probes. Modification of nucleic acid probes to allow specific bonding and/or cross-linking of captured targets can be done, for example, as illustrated in FIG. 3. This shows one of the helper strands 6 with the part that hybridizes to the thread strand DNA shown in black 8 and the part that hangs out to form the nucleic acid probe shaded gray 7. (See below for a detailed discussion of nucleic acid tiling arrays based on nucleic acid thread strands and helper strands.) One approach is to modify the nucleic acid probe by attaching a PEG-tethered psoralin molecule to one end of the nucleic acid probe. Reagents are available for doing this to, for example, DNA that is modified with an amine group at its 5' end, but other approaches can be realized as will be understood by those skilled in the art, based on the teachings herein. In this embodiment, once hybridization to the target has occurred, the array is exposed to UV light for an appropriate period of time (for example, about 15 minutes) for chemical cross linking of the target and probe. As will be apparent to those of skill in the art based on the teachings herein, similar modifications can be made using other modifications, and such modifications can be applied to any type of nucleic acid tiling array.

In a third embodiment, the nucleic acid probe strand comprises 2'-5' DNA. This is a synthetic material with a shortened backbone that has a base-spacing matching the A conformation of DNA. Thus, it does not normally hybridize with DNA in the B form, but will hybridize readily with RNA. In this embodiment, the portion of the helper strand that hybridizes with the thread strand can be made from normal DNA (ie: B-form). This product can be readily synthesized, as nucleic acid bases are available with phosphor-amadite linkages to 2'5' sugar-phosphate backbone. Thus, a DNA sequence can be readily continued into a sequence of 2'-5' DNA on a DNA synthesizer. This product may, in turn, be modified with a PEG-psoralin complex (or other modification) at its terminus, as disclosed above. Nucleic acid tiling arrays made according to this embodiment are especially preferred for use in gene expression assays. As will be apparent to those of skill in the art, similar use of 2'-5' DNA in nucleic acid probes can be made using any type of nucleic acid tiling array incorporating nucleic acid probes.

In one embodiment, the nucleic acid tiling array for use in the present invention comprises a nucleic acid thread strand-based tile, comprising:

(a) a nucleic acid thread strand;

(b) a plurality of helper nucleic acid strands that are complementary to parts of the nucleic acid thread strand; wherein a plurality of the helper nucleic acid strands further comprises a nucleic acid probe; and wherein the nucleic acid thread strand is folded into a desired shape by hybridization to the helper strands;

wherein the nucleic acid thread strand is not complementary to any of the nucleic acid probes, and wherein the predetermined size of the array is determined by the length and shape of the nucleic acid thread strand as folded by helper strands.

In a preferred embodiment, the nucleic acid thread strand, the nucleic acid helper strands, and the nucleic acid probe comprise or consist of DNA.

As used herein, "the nucleic acid thread strand is not complementary to any of the nucleic acid probes" means that the nucleic acid probes do not base pair with the thread strand over the length of the nucleic acid probe under the conditions used, and thus the helper strands are available for interactions with a target.

This embodiment provides a self-assembling, finite nucleic acid thread strand tile that allows a wide variety of discrete molecules to be placed at precise locations on the nucleic acid thread strand tile with nm-scale accuracy, and thus has widespread use in, for example, the fields of nano-electronics, nanomechanical devices, biosensors, programmable/autonomous molecular machines, and molecular computing systems. Thus, in a further embodiment, the nucleic acid thread strand tile further comprise a plurality of targets bound to nucleic acid probes specific for those targets.

The nucleic acid thread strand can be any suitable polynucleotide of appropriate length and sequence for the desired nucleic acid tile. In one embodiment, the nucleic acid thread strand is a genomic nucleic acid strand, or suitable fragments thereof, such as from a virus, bacterium, or indeed any organism from which long DNA can be extracted. The only caveat is that the chosen section of genomic nucleic acid should not have sequences that are complementary to the probe sequences, and they should not contain significant amounts of repeated sequences or other sequences that might form structures that interfere with assembly of the array (such the G-rich regions that might form quadruplexes as in telomere DNA).

In one embodiment, genomic nucleic acid, or fragments thereof, is used as the nucleic acid thread for lengths above about 50 bp where synthetic nucleic acid becomes expensive and difficult to make. Lengths up to the full length of an organism's genome (ca. $10^9$ bp) are feasible if they met the sequence criteria described above.

The nucleic acid helper strands are complementary to regions of the nucleic acid thread and not to each other, and are designed to hybridize to the nucleic acid thread strand so as to constrain the nucleic acid thread strand into a desired shape. A plurality of the nucleic acid helper strands comprise nucleic acid probes. In one embodiment, helper strands are between 10 and 50 nucleotides, not including any DNA probe that is part of the helper strand.

In a further embodiment, the nucleic acid thread-based tile further comprises nucleic acid filler strands that hybridize to the nucleic acid thread strand. These strands are not involved in shaping the nucleic acid thread strand, but add further structural integrity to the resulting nucleic acid tile. It is further preferred that a plurality of the nucleic acid filler strands further comprises a nucleic acid probe. In a further preferred embodiment, the nucleic acid filler strands comprise or consist of DNA.

In an even more preferred embodiment, each of the nucleic acid probes on the nucleic acid thread-based tile are unique, thus providing a large number of unique probes on the nucleic acid tile. In a further preferred embodiment, the single nucleic acid tile array comprises target bound to the nucleic acid probe. In various further preferred embodiments, the target can be any target as described above, including but not limited to DNA, RNA, polypeptides, lipids, carbohydrates, other organic molecules, inorganic molecules and metallic particles, magnets, and quantum dots.

Figure 1:
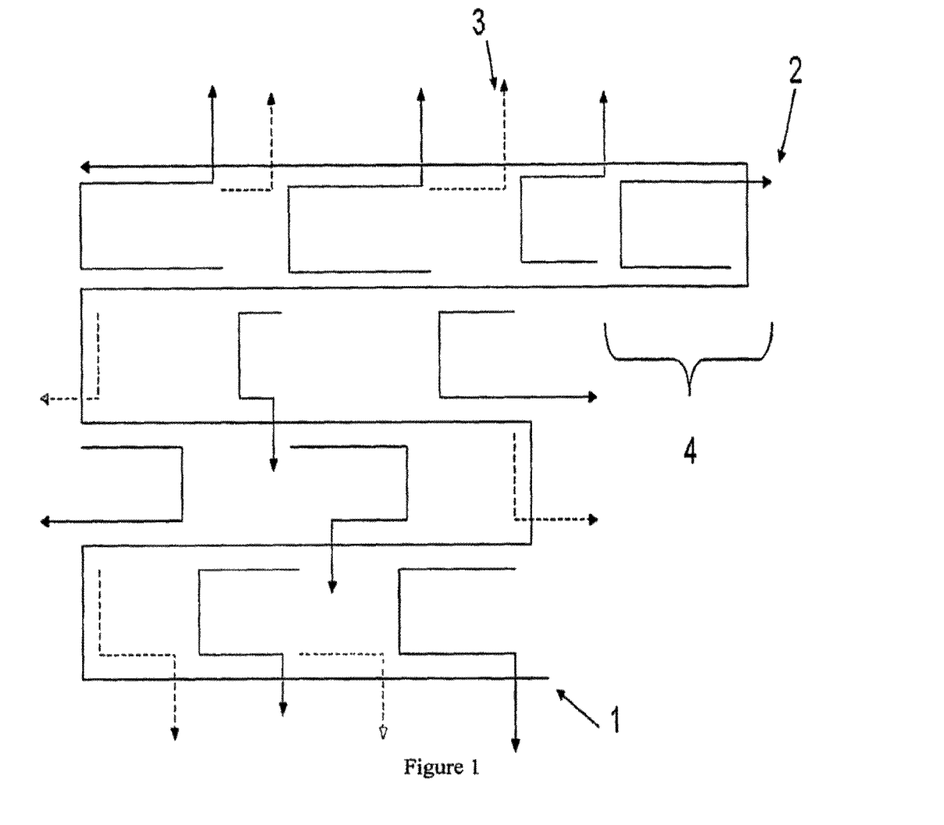
FIG. 1 is a diagram of an exemplary DNA thread-based tile.

FIG. 1 provides an exemplary DNA thread-based tile. The threaded array (1) is a large piece of genomic DNA chosen to have no overlapping sequences that are complements of the probes. For example, if human sequences are the target, the DNA thread strand (1 in FIG. 1) could be an appropriately long viral genome. The DNA thread strand is folded into the desired shape (here a rectangle with a protruding indexing feature on the upper left) by helper strands, each chosen to go to the desired position in the array, and one or more of them bearing DNA probes. The helper strands are chosen to cross-link the scaffold strand (1) by hybridization and the formation of cross over structures, as shown by the strands in FIG. 16 (2 is an example). Other filler strands (also possibly carrying DNA probes) fill out the array and strengthen it (dashed strands exemplified by 3). The array carries an asymmetric indexing feature for imaging, here the piece labeled 4.

In another embodiment, one or more of the helper strands can be part of a larger nucleic acid structure. In one example, one or more helper strands protrude from one or more nucleic acid tiles. In a further embodiment, all of the helper strands in the thread strand-based tile protrude from individual nucleic acid tiles.

In another embodiment, one or more of the helper strands may protrude from one or more nucleic acid arrays (formed by combining two or more nucleic acid tiles), including but not limited to those disclosed above. In this embodiment, one or more helper strands protrude from one or more tiling arrays and fold the thread strand into place, and the tiling arrays (and the nucleic acid tiles they are composed of, including nucleic acid probes) comprising the helper strands are thus precisely positioned on the thread strand. In this embodiment, it is possible, for example, to provide unlimited hierarchies of nucleic acid tiling arrays. In a preferred embodiment, all of the helper strands in the thread strand-based tile protrude from nucleic acid arrays.

The dimensions of a given nucleic acid thread strand-based tile can be programmed, based on the available length and sequence of thread strand nucleic acid, and other design elements. For example, a 10,000 base thread strand nucleic acid could be formed into a nucleic acid tile covering an area of approximately 2 nm×10,000×0.3 nm or $6 \times 10^{-15}$ m$^2$. This would correspond to a square of about 0.1 µm on each side. Depending upon the design of the thread strand-based nucleic acid tile, the size of the nucleic acid probe, the specific target, and other design feature, the density of target molecules on the nucleic acid tile can be as high as $10^{12}$ per square cm.

In one embodiment, the nucleic acid thread-based tile can be assembled in one step. A long template strand of nucleic acid is mixed with shorter 'helper' strands, usually in a large molar excess of the shorter strands. The strand sequences are chosen to fold the long template strand into the desired shape, as described by Yan et al. (Proceedings of the National Academy of Sciences 100, Jul. 8, 2003 pp 8103-8108.) The probe array is then achieved by using one or more helper strands with nucleic acid probes that are not complementary to any part of the template strand or the other helper strands. These will then protrude from the array, forming single stranded probe strands at known locations if the array contains an index feature as described earlier. General conditions for such hybridization are as disclosed above for the second aspect of the invention except that it is preferable to use a large molar excess of the helper strands in this approach.

As a specific example of preparation of the high-density DNA tile self-assembled around single strand long viral genome DNA scaffolds: Viral DNA such as M13 can be purchased from New England Biolabs. The circular single stranded DNA is then digested into a single strand using restriction enzyme cleavage at selected sites by hybridizing a short complementary strand at the restriction enzyme recognition site. All the short DNA helper strands are added to a solution containing the long scaffold strand in a ratio of 100:1 (large excess of helper strand) with the scaffold concentration at 1 nM. This ensures the helper strands goes into the array with a high yield. The arrays are annealed in 1×TAE/Mg buffer (40 mM Tris, 20 mM acetic acid, 2 mM EDTA, and 12.5 mM magnesium acetate, pH 8.0). The mixture solution is cooled slowly from 90° C. to 20° C. Monitoring to ensure correct assembly is carried out as described for the second aspect of the invention.

In another embodiment (or as part of the above embodiment), the nucleic acid tiling array comprises a plurality of nucleic acid tiles joined to one another via sticky ends, wherein each nucleic acid tile comprises one or more sticky ends, and wherein a sticky end for a given nucleic acid tile is complementary to a single sticky end of another nucleic acid tile in the nucleic acid tiling array; wherein the nucleic acid tiles are present at predetermined positions within the nucleic acid tiling array as a result of programmed base pairing between the sticky ends of the nucleic acid tiles. In a further embodiment, the nucleic acid comprises or consists of DNA (ie: the nucleic acid tiling array comprises a DNA tiling array, with a plurality of DNA tiles, etc.) As used herein, "programmed base pairing" means that the sticky ends for the different nucleic acid tiles are designed to ensure interactions of specific nucleic acid tiles through their complementary sticky ends, thus programming the position of the nucleic acid tile within the nucleic acid tiling array. As used herein, "predetermined positions" means that the ultimate position of each nucleic acid tile in the self-assembled nucleic acid tiling array is based on the sequence and position of its sticky ends and the sequence and position of the sticky ends of the other nucleic acid tiles in the nucleic acid tiling array, such that the plurality of nucleic acid tiles can only assemble in one specific way. Since the position of all nucleic acid tiles in the array is predetermined, the boundary tiles are also predetermined, and thus the nucleic acid tiling arrays of the present invention have defined boundaries (ie: "finite" nucleic acid tiling arrays). In this embodiment, each "nucleic acid tile" comprises (a) a structural element (also referred to herein as the polynucleotide "core") constructed from a plurality of nucleic acid polynucleotides; and (b) 1 or more "sticky ends" per nucleic acid tile attached to the polynucleotide core. Those of skill in the art are well aware of the wide range of such polynucleotide cores, including but not limited to those disclosed above. The choice of which nucleic acid tile type to use is also within the level of skill in the art, based on the teachings herein and the desired use. For example, an assembly of 4 arm branch junctions would prove useful for displaying small arrays of peptides, whereas an array based on a long threading strand may prove useful for large gene-expression arrays. Self-assembly of a plurality of nucleic acid tiles results in programmed base-pairing interactions between sticky ends on different nucleic acid tiles to form nucleic acid tiling arrays. As used herein, a "plurality" of nucleic acid tiles means 4 or more nucleic acid tiles. In various preferred embodiments, the nucleic acid tiling array contains at least 6, 9, 16, 25, 36, 49, 64, 81, 100, 121, 144, 169, 206, 225, 256, 289, 324, 361, or 400 nucleic acid tiles As used herein, a "nucleic acid tiling array" is the assembled array of nucleic acid tiles of the invention based on specific Watson-Crick base pairing between sticky ends of different nucleic acid tiles. Each nucleic acid tile within the nucleic acid tiling array is located at a pre-determined position in the array, based on the complementarity of its "sticky ends" to sticky ends on a different nucleic acid tile. As will be apparent to those of skill in the art, a given nucleic acid tile may specifically bind to only one other nucleic acid tile in the nucleic acid tiling array (if the given nucleic acid tile is programmed with only a single sticky end), or it may interact with 2, 3, 4, 5, 6, 7, 8, 9, 10, 11, 12, or more other nucleic acid tiles in the nucleic acid tiling array if the given nucleic acid tile has 2, 3, 4, 5, 6, 7, 8, 9, 10, 11, 12, or more sticky ends, respectively. For example, closely packed arrays typically utilize 2-12 sticky ends, but more sticky ends might be used in an array that branched from a central point, as in a dendrimeric nucleic acid tiling array.

As used herein, a "sticky end" is a single stranded base sequence attached to the polynucleotide core of a nucleic acid tile. For each sticky end, there is a complementary sticky end on a different nucleic acid tile with which it is designed to bind, via base pairing, within the nucleic acid tiling array. Each nucleic acid tile must contain at least one sticky end, but may contain 2, 3, 4, 5, 6, 7, 8, 9, 10, 11, 12, or more sticky ends, depending on the design of the nucleic acid tiling array. The sticky ends are incorporated into the nucleic acid tile as a portion of one or more of the core polynucleotides. It will be apparent to those of skill in the art, based on the teachings herein, that such incorporation can be carried out in a variety of ways, in part depending on the type of polynucleotide core used. As will be understood by those of skill in the art, the specific nucleic acid sequence of the core polynucleotides and sticky ends shown in the Figures is not a limitation of the present invention; the only sequence requirement is that a set of complementary polynucleotides capable of base-pairing be used.

The length of the sticky ends for each nucleic acid tile can vary, depending on the desired spacing between nucleic acid tiles, the number of nucleic acid tiles in the nucleic acid tiling array, the desired dimensions of the nucleic acid tiling array, and any other design parameters such as the desired distance between ligands attached to the array or between probes and ligands that might bind more than one probe cooperatively. The sticky ends do not have to be of identical length for a given nucleic acid tile or relative to other nucleic acid tiles in the nucleic acid tiling array, so long as a complementary sticky end of an identical length is present on the nucleic acid tile to which it is designed to base pair. Alternatively, the sticky ends on all of the nucleic acid tiles can be of identical length. Particularly preferred lengths of the sticky ends are 4, 5, 6, 7, 8, 9, or 10 nucleotides.

In one embodiment of this first aspect, each sticky end for a given nucleic acid tile is (a) different than the other sticky ends for that nucleic acid tile; (b) unique to that nucleic acid tile with respect to all other nucleic acid tiles in the array; and (c) complementary to a single sticky end of one other nucleic acid tile in the nucleic acid tiling array. As will be apparent to those of skill in the art, the polynucleotide structural element of each nucleic acid tile can be identical in this embodiment, so long as the sticky ends are unique. Thus, in this embodiment, a nucleic acid tiling array with "N" tiles is made by synthesizing "N" different tiles, each containing unique sticky-ends to connect to its neighboring tiles, so that each tile takes up a unique and well defined position in the array.

In a preferred embodiment of this first aspect of the invention, the nucleic acid tiles are not all unique (i.e.: some of the nucleic acid tiles may contain the same sticky ends). The nucleic acid tiling strategy in this embodiment takes advantage of the geometric symmetry of the nucleic acid tiling array. In general, to use a total of N tiles to construct a fixed size 2D nucleic acid tiling array with $C_m$ symmetry, where m=2, 3, 4, or 6, the number of unique tiles the fixed size array requires is N/m, if N/m is an integral number, or Int (N/m)+1, if N/m is an non-integral number. This strategy is cost-effective in material, particularly when combined with embodiments where the polynucleotide structural element for each nucleic acid tile is identical. This embodiment minimizes polynucleotide design time and the sample preparation time dramatically. In these embodiments, the total number of unique sticky end pairs is preferably N*(N−1)/2.

In certain applications, a particular symmetry may prove valuable. For example, if the arrays are designed to hold metal particles for photonic arrays, one type of structure might be a ring array of metal spheres. In that case, a nucleic acid lattice of $C_n$ (where n is equal to or greater than 6) would be valuable. In a preferred embodiment of this first aspect, the resulting nucleic acid tiling array is "non-periodic," meaning that the array does not include simple repetitive nucleic acid tile "patterns," such as ABABAB; ABCDABCD; ABABDCD-CABABDCDC. As disclosed above, this does not require that all of the tiles in the array be unique. The formation of non-periodic nucleic acid nanoarrays has been a major challenge in nanotechnology and this embodiment of the invention provides numerous potential applications for nanofabrication of complex structures and useful devices.

The dimensions of a given nucleic acid tile can be programmed, based on the length of the core polynucleotides and their programmed shape and size, the length of the sticky ends, and other design elements. Based on the teachings herein, those of skill in the art can prepare nucleic acid tiles of any desired size. In a preferred embodiment the length and width of individual nucleic acid tiles are between 3 nm and 50 nm, more preferably between 6 nm and 30 nm, and even more preferably between 7 nm and 20 nm.

The dimensions of the resulting nucleic acid tiling array can also be programmed, depending on the size of the individual nucleic acid tiles, the number of nucleic acid tiles, the length of the sticky ends, the desired spacing between individual nucleic acid tiles, and other design elements. Based on the teachings herein, those of skill in the art can prepare nucleic acid tiling arrays of any desired size, including arrays of at least 1-10 μm in length.

Synthesis of polynucleotides is well known in the art. It is highly desirable, but not essential, in making the polynucleotides for the nucleic acid tiles to appropriately design sequences to minimize undesired base pairing and undesired secondary structure formation. Computer programs for such purposes are well known in the art. (See, for example, Seeman, N. C., J Biomol Struct Dyn, 1990. 8: p. 573-81). It is further preferred that the polynucleotides are purified prior to nucleic acid tile assembly. Purification can be by any appropriate means, such as by gel electrophoretic techniques.

The nucleic acid tiling arrays may be present in solution, in lyophilized form, or attached to a substrate. Non-limiting examples of substrates to which the nucleic acid tiling arrays can be attached include silicon, quartz, other piezoelectric materials such as langasite ($La_3Ga_5SiO_{14}$), nitrocellulose, nylon, glass, diazotized membranes (paper or nylon), polyformaldehyde, cellulose, cellulose acetate, paper, ceramics, metals, metalloids, semiconductive materials, coated beads, magnetic particles; plastics such as polyethylene, polypropylene, and polystyrene; and gel-forming materials, such as proteins (e.g., gelatins), lipopolysaccharides, silicates, agarose and polyacrylamides.

The nucleic acid tiling arrays of the invention can be attached to such surfaces using any means in the art. For example, one simple way to do this is with multiply charged cations (Mg, Ni, Cu etc.) that spontaneously attach to a negative surface like glass or mica, leaving extra charge to attach the nucleic acid. Another way to do this is with singly charged cations that are tethered to the surface chemically. An example would be aminopropyltriethoxysilane reacted with a surface containing hydroxyl groups. This attached to oxide surfaces by hydrolysis of the silanes, and leaves a positively charged amino group on the surface at neutral pH.

In a second aspect, the present invention provides methods for gene expression analysis, comprising incubating a sample containing mRNA to be analyzed with one or more nucleic acid tiling arrays according to the third embodiment of the first aspect of the invention, under conditions wherein the 2'-5'-containing nucleic acid probes can hybridize with mRNA targets in the sample, followed by isolation of the nucleic acid tiling arrays and analysis of binding events on the arrays. The use of the modified 2'-5' DNA prevents accidental hybridization with DNA.

The sample can be any sample containing mRNA, but preferably comprises disrupted cells, cell lysates, blood, serum, saliva, and urine. Once hybridized with the array, RNA probes are stable against RNAse digestion. In a preferred embodiment, a chelating agent is used in the hybridization buffer to remove divalent ions in the hybridization buffer that are required by, for example, RNAse H.

In a preferred embodiment of this second aspect of the invention, the nucleic acid probes are chemically modified, such as by biotin, according to the first embodiment of the first aspect of the invention. After incubation to promote hybridization to target mRNA, streptavidin coated beads, or their equivalents, are incubated with the mixture to facilitate isolation of the nucleic acid tiling arrays prior to analysis of binding events. In a further embodiment, the streptavidin-coated beads can be washed to remove unbound material, such as unbound nucleic acids, cell lysate, etc. In a further embodiment, the cells can be lysed and the lysate incubated with a solution of the arrays. Since solutes on the order of 100 fl are easily handled by microinjectors (such as the FemtoJect from Eppendorf) this approach allows detection of very small amounts of material. For example, it is easily possible to visualize $10^9$ arrays in 2 microliters with an atomic force microscope (AFM). Using the femto-injector referred to above permits the use of just 50 arrays ($10^{-13} \times 10^9 / 2\,\mu l$). Thus, gene expression from just a single cell (with a copy number of >50) is detectable. The concentration of analytes in such a mix exceeds the affinity constant of a 40 bp hybrid by many orders of magnitude.

In a further preferred embodiment of this second aspect, the nucleic acid probes further comprise a PEG-psoralin complex (or other modification) at its terminus, as disclosed above in the second embodiment of the first aspect of the invention. In this embodiment, the hybridization mixture is exposed to UV light for a time sufficient (for example, 15 minutes) to drive the psoralin cross linking reaction of the 2'-5'DNA probe to the target mRNAs. This embodiment provides an improved stability of the hybridization products on the nucleic acid tiling arrays, which improves detection.

The nucleic acid tiling arrays are small enough that many thousands of arrays can easily be injected to a single cell or mixed with a lysate from a single cell, thus permitting detection of mRNA expression in single cells.

In a most preferred embodiment of this second aspect, the method comprises (a) Incubating disrupted cells with biotin-modified nucleic acid tiling arrays comprising nucleic acid probes comprising 2'-5' DNA and PEG-tethered psoralin molecule attached to one or more nucleic acid probe on the nucleic acid tiling array, to hybridize with m-RNA from the cytoplasm. The use of the modified 2'-5' DNA prevents accidental hybridization with DNA. The arrays are small enough that many thousands of arrays can easily be injected to a single cell or mixed with a lysate from a single cell.

(b) The reaction mixture is exposed to UV light for approximately 15 minutes to drive the psoralin cross linking reaction of the 2'-5'DNA probe to the target mRNAs.

(c) The resulting material is incubated with streptavidin coated beads. This reaction can be carried out in the very small volumes characteristic of a single cell lysate. Preferably, the beads would be tethered to the surface of a microtiter plate or microfluidic chip.

(d) The arrays are bound to the surface tethered beads, so the cell-lysate products can be rinsed away.

(e) The arrays may be released from the bead surface by incubation with a large excess of biotin.

(f) The resulting pure solution of arrays with bound targets may then be placed onto a functionalized surface, including but not limited to a nickel treated mica surface, to bind the arrays, as is known to those of skill in the art. This can be done by contacting the mica with the small drop of product in the microtiter well, or by moving the product to the imaging substrate by microfluidic means.

The arrays may then be read out by, for example, atomic force microscopy, or other appropriate detection methods, as previously described. (See, for example, Lindsay, The scanning probe microscope in biology in Scanning Probe Microscopy, techniques and Applications-2nd edition edited by D. Bonnell, Wiley, NY 2000.) Based on the teachings herein, it will be apparent to one of skill in the art, that the entire process described in the above step could be carried out on one very simple microfluidic platform of at least three chambers. One chamber would be used to mix cell lysate (or other analyte) with arrays. A second chamber would be used for extraction of the arrays and rinsing off of the remains of the cell-lysate (or other analyte). A third chamber would comprise a flat surface, indexed to fit into an atomic force microscope and treated, so as to bind the arrays for imaging.

We claim:

1. A finite, addressable, and self-assembling nucleic acid tiling array of predetermined size comprising:
   (a) one or more nucleic acid tiles, wherein each nucleic acid tile in the nucleic acid tiling array comprises a plurality of nucleic acid probes capable of binding to a target, wherein the nucleic acid probes are attached at predetermined locations on the nucleic acid tile;
   (b) an indexing feature; wherein the nucleic acid tiling array is of a predetermined size;
   (c) a nucleic acid thread strand;
   (d) a plurality of helper nucleic acid strands that are complementary to the nucleic acid thread strand; wherein a plurality of the helper nucleic acid strands further comprises a nucleic acid probe; and wherein the nucleic acid thread strand is folded into a desired shape by hybridization to the helper strands; wherein the nucleic acid thread strand is not complementary to any of the nucleic acid probes, and wherein the predetermined size of the array is determined by the length and shape of the nucleic acid thread strand; and
   (e) nucleic acid filler strands that hybridize to the nucleic acid thread strand, wherein the nucleic acid filler strands are not involved in shaping the nucleic acid thread strand, but add further structural integrity to the resulting nucleic acid tile;
   wherein the nucleic acid tiling array comprises one or more of the following:
   (i) an addressable nucleic acid probe and one or more unique chemical tags;
   (ii) one or more nucleic acid probes on the nucleic acid tiling array modified to permit specific bonding and/or cross-linking of captured targets to the nucleic acid probes; and (iii) addressable nucleic acid probes, wherein one or more of the nucleic acid probes comprises 2'-5' DNA.

2. The finite, addressable and self-assembling nucleic acid array of claim 1, wherein the nucleic acid probes comprise pairs of single stranded nucleic acids arranged to permit a pair of single stranded nucleic acids to both hybridize to the same target.

3. The finite, addressable and self-assembling nucleic acid array of claim 2, wherein the pair of single stranded nucleic acids are arranged to permit formation of a continuous double helix after hybridization to the target.

4. The nucleic acid tiling array of claim 1, wherein a plurality of the nucleic acid filler strands further comprises a nucleic acid probe.

5. The nucleic acid tiling array of claim 1 wherein each of the nucleic acid probes is unique.

6. The nucleic acid tiling array of claim 1, wherein the target is selected from the group consisting of DNA, RNA, polypeptides, lipids, carbohydrates, other organic molecules, inorganic molecules and metallic particles, magnets, and quantum dots.

7. The nucleic acid tiling array of claim 6, further comprising bound ligand.

8. The nucleic acid tiling array of claim 7, wherein the bound ligand is selected from the group consisting of DNA, RNA, polypeptides, lipids, carbohydrates, other organic molecules, inorganic molecules and metallic particles, magnets, and quantum dots.

9. The finite, addressable and self-assembling nucleic acid array of claim 1, wherein the nucleic acid tiling array comprises the addressable nucleic acid probe and one or more unique chemical tags.

10. The finite, addressable and self-assembling nucleic acid array of claim 1, wherein the nucleic acid tiling array comprises the one or more nucleic acid probes on the nucleic acid tiling array modified to permit specific bonding and/or cross-linking of captured targets to the nucleic acid probes.

11. The finite, addressable and self-assembling nucleic acid array of claim 1, wherein the nucleic acid tiling array comprises the addressable nucleic acid probes, wherein one or more of the nucleic acid probes comprises 2'-5' DNA.

* * * * *

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
gtacgtacga aaaacctaac g                                         21

<210> SEQ ID NO 2
<211> LENGTH: 22
<212> TYPE: DNA
<213> ORGANISM: Artificial Sequence
<220> FEATURE:
<223> OTHER INFORMATION: Synthetic

<400> SEQUENCE: 2
catgcatgca tttttggatt gc                                        22
```